US009311529B2

(12) United States Patent
Fukasawa

(10) Patent No.: US 9,311,529 B2
(45) Date of Patent: Apr. 12, 2016

(54) IMAGE PROCESSING APPARATUS, IMAGE PROCESSING METHOD, AND NON-TRANSITORY COMPUTER READABLE MEDIUM

(71) Applicant: FUJI XEROX CO., LTD., Minato-ku, Tokyo (JP)

(72) Inventor: Tetsuo Fukasawa, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 1 day.

(21) Appl. No.: 14/462,063

(22) Filed: Aug. 18, 2014

(65) Prior Publication Data
US 2015/0254506 A1 Sep. 10, 2015

(30) Foreign Application Priority Data

Mar. 5, 2014 (JP) .................................. 2014-042820

(51) Int. Cl.
*G06K 9/00* (2006.01)
*A61B 6/00* (2006.01)
*G06F 19/00* (2011.01)

(52) U.S. Cl.
CPC .......... *G06K 9/00449* (2013.01); *A61B 6/5294* (2013.01); *G06F 19/322* (2013.01)

(58) Field of Classification Search
USPC ................................................ 382/128–134
See application file for complete search history.

(56) References Cited

U.S. PATENT DOCUMENTS

| 5,740,428 | A | * | 4/1998 | Mortimore | ............ G06F 19/321 |
| 5,982,953 | A | * | 11/1999 | Yanagita | ............... G06F 19/321 348/580 |
| 6,269,379 | B1 | * | 7/2001 | Hiyama | .................... G06T 3/40 |
| 2003/0194121 | A1 | * | 10/2003 | Eberhard | ............... A61B 6/463 382/132 |
| 2003/0229299 | A1 | * | 12/2003 | Shimura | ............... G06T 7/0012 600/595 |
| 2004/0101188 | A1 | * | 5/2004 | Oosawa | .................. G06T 7/001 382/132 |
| 2005/0141757 | A1 | * | 6/2005 | Ayache | ................. G06T 7/0012 382/128 |
| 2005/0192838 | A1 | * | 9/2005 | Jones | .................... G06F 19/322 705/2 |
| 2005/0251020 | A1 | * | 11/2005 | Kondo | .................. G06F 19/321 600/407 |
| 2006/0239530 | A1 | * | 10/2006 | Oosawa | ............... G06T 7/0012 382/130 |
| 2007/0115999 | A1 | * | 5/2007 | Qu | ........................ G06F 19/321 370/392 |
| 2009/0100321 | A1 | * | 4/2009 | Singh | .................... G06F 3/0482 715/205 |
| 2010/0046842 | A1 | * | 2/2010 | Conwell | ........... G06F 17/30265 382/218 |

FOREIGN PATENT DOCUMENTS

JP 63-131282 A 6/1988
JP 09-044585 A 2/1997

* cited by examiner

*Primary Examiner* — Alex Liew
(74) *Attorney, Agent, or Firm* — Sughrue Mion, PLLC

(57) ABSTRACT

An image processing apparatus includes an extractor that receives sheet image data that is generated by reading an image on a medical record sheet onto which basic medical information and encoded information of the basic medical information are printed, and extracts, from the sheet image data, information image data representing a portion where the basic medical information is printed, an image generator that generates reference image data representing the basic medical information, based on the encoded information represented in the sheet image data, and a detector that detects a correction that is to be performed on the basic medical information printed on the medical record sheet, based on a difference between the information image data and the reference image data.

19 Claims, 12 Drawing Sheets

FIG. 2

```
100
 ┌─────────────────────────────────────────────┐
 │  PATIENT ID:        00001            [QR]104│
 │  PATIENT NAME:      Taro FUJI               │
 │102 SERVICES:        INTERNAL MEDICINE       │
 │  DOCUMENT TYPE:     PATIENT REFERRAL        │
 │                     DOCUMENT                │
 │  EXAMINATION DATE:  2013/11/08̶ 09           │
 │                                  ↖106       │
```

PATIENT ID: 00001
PATIENT NAME: Taro FUJI
SERVICES: INTERNAL MEDICINE
DOCUMENT TYPE: PATIENT REFERRAL DOCUMENT
EXAMINATION DATE: 2013/11/~~08~~ 09

MEDICAL INTERVIEW SHEET
EXAMINATION DATE: NOVEMBER 9, 2013

| NAME | Taro FUJI | HEIGHT | 169 |
|------|-----------|--------|-----|
| AGE  | 23        | WEIGHT | 60  |
| SEX  | MALE      |        |     |

FIG. 3

| SHEET ID | START POINT (TOP LEFT) [pixel] | END POINT (BOTTOM RIGHT) [pixel] |
|---|---|---|
| 1 | (20, 20) | (400, 200) |
| 2 | (30, 30) | (410, 210) |
| 3 | (10, 40) | (390, 220) |

FIG. 4

| SHEET ID | INFORMATION | ITEM | START POINT (TOP LEFT) [pixel] | END POINT (BOTTOM RIGHT) [pixel] |
|---|---|---|---|---|
| 1 | PATIENT ID | ID | (20, 20) | (200, 40) |
| | PATIENT NAME | FAMILY NAME | (20, 40) | (200, 80) |
| | | GIVEN NAME | (200, 40) | (400, 80) |
| | SERVICES | SERVICES | (20, 80) | (400, 100) |
| | DOCUMENT TYPE | DOCUMENT TYPE | (20, 100) | (400, 120) |
| | EXAMINATION DATE | YEAR | (20, 120) | (200, 200) |
| | | MONTH | (200, 150) | (300, 200) |
| | | DAY | (300, 180) | (400, 200) |

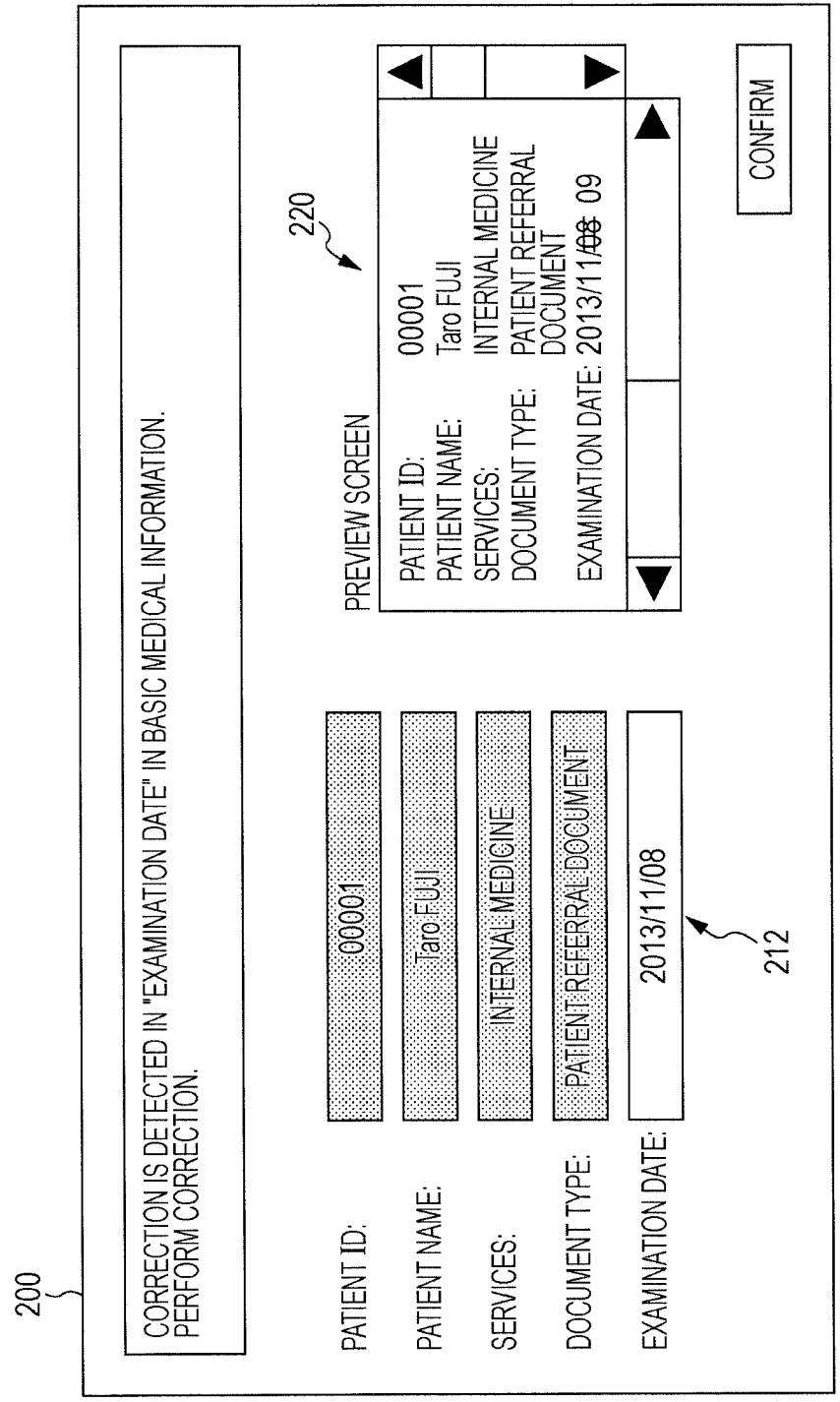

FIG. 9

CORRECTION IS DETECTED IN "DAY" OF EXAMINATION DATE IN BASIC MEDICAL INFORMATION.
PERFORM CORRECTION.

PATIENT ID: 00001
PATIENT NAME: Taro FUJI
SERVICES: INTERNAL MEDICINE
DOCUMENT TYPE: PATIENT REFERRAL DOCUMENT
EXAMINATION DATE: 2013/11 08

PREVIEW SCREEN

PATIENT ID: 00001
PATIENT NAME: Taro FUJI
SERVICES: INTERNAL MEDICINE
DOCUMENT TYPE: PATIENT REFERRAL DOCUMENT
EXAMINATION DATE: 2013/11/~~08~~ 09

CONFIRM

IMAGE PROCESSING APPARATUS, IMAGE PROCESSING METHOD, AND NON-TRANSITORY COMPUTER READABLE MEDIUM

CROSS-REFERENCE TO RELATED APPLICATIONS

This application is based on and claims priority under 35 USC 119 from Japanese Patent Application No. 2014-042820 filed Mar. 5, 2014.

BACKGROUND (i) Technical Field

The present invention relates to an image processing apparatus, an image processing method, and a non-transitory computer readable medium.

(ii) Related Art

In the medical field, information of a medical record sheet is digitized by reading an image of the medical record sheet, such as a medical record card, and digitized image data is stored on a shared server for information sharing purposes.

Basic medical information, such as a patient name and a date of examination, may be coded, and the coded information may be printed on a medical record sheet. The basic medical information itself may be printed to clearly indicate the medical information. In such a case, the coded information may be decoded to generate the basic medical information when the medical record sheet is digitized. The image data of the medical record sheet is managed in accordance with the decoded basic medical information.

SUMMARY

According to an aspect of the invention, an image processing apparatus is provided. The image processing apparatus includes an extractor that receives sheet image data that is generated by reading an image on a medical record sheet onto which basic medical information and encoded information of the basic medical information are printed, and extracts, from the sheet image data, information image data representing a portion where the basic medical information is printed, an image generator that generates reference image data representing the basic medical information, based on the encoded information represented in the sheet image data, and a detector that detects a correction that is to be performed on the basic medical information printed on the medical record sheet, based on a difference between the information image data and the reference image data.

BRIEF DESCRIPTION OF THE DRAWINGS

Exemplary embodiments of the present invention will be described in detail based on the following figures, wherein:

FIG. 2 illustrates an example of a medical record sheet;

FIG. 3 illustrates an example of a print area management table;

FIG. 4 illustrates an example of the print area management table;

FIG. 8 illustrates an example of the screen to modify the basic medical information;

FIG. 9 illustrates an example of the screen to modify the basic medical information;

DETAILED DESCRIPTION

Figure 1:
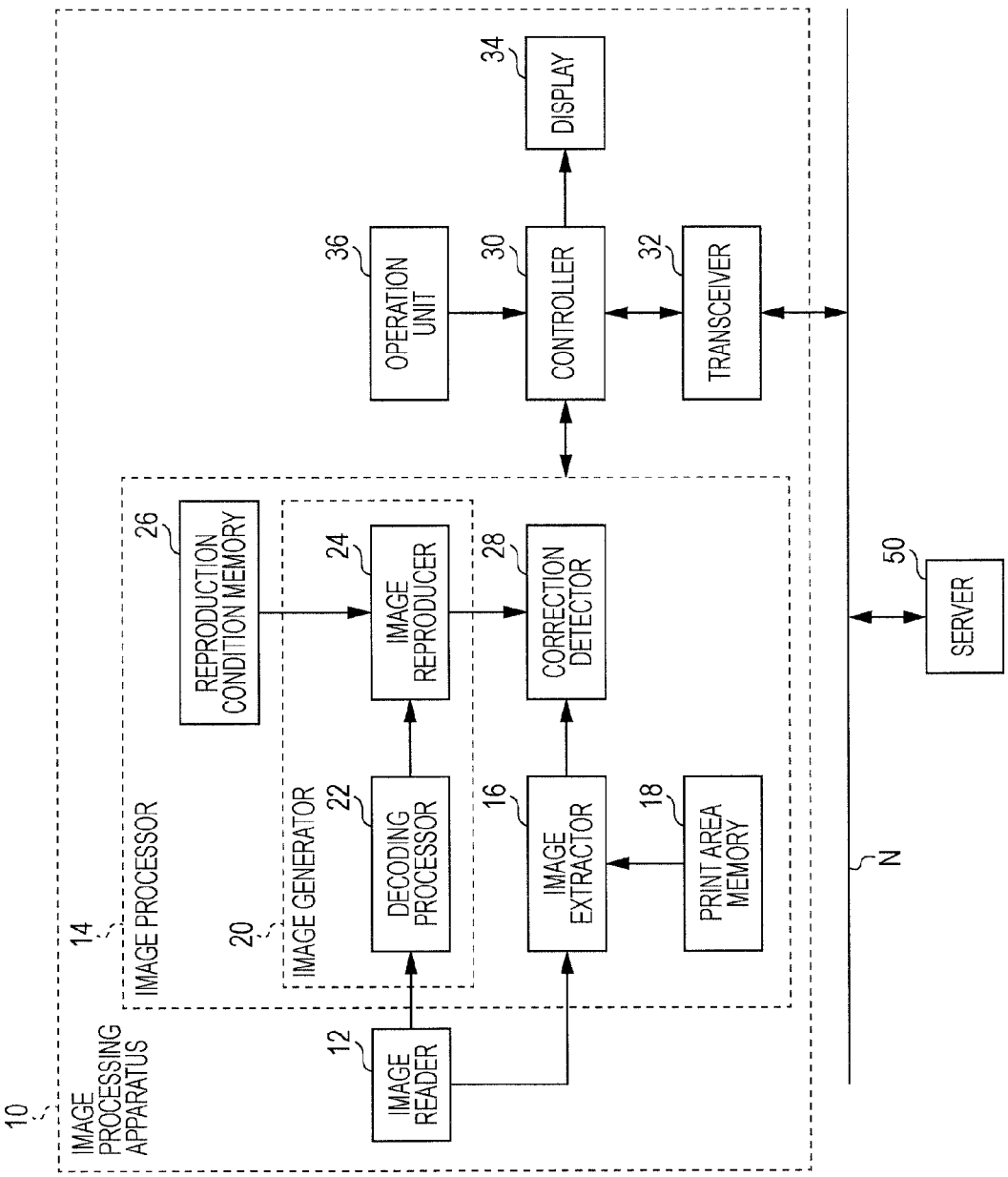
FIG. 1 is a block diagram illustrating an example of an image processing apparatus of an embodiment of the present invention.

FIG. 1 illustrates an image processing apparatus 10 of an embodiment of the present invention. The image processing apparatus 10 is connected to a server 50 via a communication network N. As described in detail below, the image processing apparatus 10 generates medical record sheet image data by reading an image on a medical record sheet and transmits the medical record sheet image data to the server 50 through the communication network N. The medical record sheet is a sheet for use in a medical institution, such as a hospital. The medical record sheets include a medical chart, an examination record sheet, a care record sheet, and a prescription.

Management information to manage the medical record sheet and the medical record image data is pre-printed on the medical record sheet. The management information includes the basic medical information and encoded information (code information). The basic medical information indicates items including a patient identification (ID) of a patient, a patient name, services, and a date of medication examination. Character strings indicating each item of the basic medical information are printed in a print area preset in accordance with a preset print expression condition in the medical record sheet. The print expression condition includes the order of the print location of each item, the layout of the print location, the type of a font of the character string, the size of the font, and the positional relationship of the character strings. The print expression condition and the print area may be different depending on the type of the medical record sheet. The encoded information is information that is generated by encoding the basic medical information in accordance with a preset encoding condition. For example, the encoded information is an encoded two-dimensional barcode that is printed on the medical record sheet. When the medical record sheet image data is generated by reading the image on the medical record sheet, the encoded information is decoded to generate decoded basic medical information (decoded information). The decoded basic medical information indicates the basic medical information printed on the medical record sheet. The medical record sheet image data is managed in accordance with the decoded basic medical information. Elements of the image processing apparatus 10 are described below.

An image reader 12 is an image reading device, such as a scanner or a digital camera. The image reader 12 generates digital image data by reading the image on the medical record sheet. In the present embodiment, the image reader 12 generates the medical record sheet image data representing the medical record sheet by reading the image on the medical record sheet.

An image processor 14 includes an image extractor 16, a print area memory 18, an image generator 20, a reproduction condition memory 26, and a correction detector 28.

The image extractor 16 extracts (slices), from the medical record sheet image data generated by the image reader 12, medical record sheet image data representing a portion where the basic medical information is printed on the medical record sheet. The medical record sheet image data is output to the correction detector 28. For example, the basic medical information is printed on a print area preset on the medical record sheet. The image extractor 16 extracts, from the medical record sheet image data, image data representing a portion corresponding to the print area as basic medical information image data. If the print area is different depending on the type of the medical record sheet, the image extractor 16 extracts, as the basic medical information image data, the image data representing the portion corresponding to the print area depending on the type of the medical record sheet. The image extractor 16 individually extracts, from the medical record sheet image data, item image data corresponding to each item of the basic medical information.

The print area memory 18 pre-stores print area information indicating the print area of the basic medical information. For example, the print area memory 18 stores the print area information on a per type basis of the medical record sheet. The print area information indicating the print area of each time may be stored on the print area memory 18. The image extractor 16 extracts the basic medical information image data in accordance with the print area information stored on the print area memory 18.

The print area memory 18 may not be necessarily included in the image processing apparatus 10. For example, the print area information may be stored on the server 50. In such a case, the image extractor 16 retrieves from the server 50 the print area information to extract the basic medical information image data and item image data. Optionally, the print area information may be encoded together with the basic medical information and included in the encoded information. In such a case, the image extractor 16 extracts the basic medical information image data and item image data based on the print area information that is generated by decoding the encoded information. As described below, the item image data serves as basic data in a detection operation, in which the presence of a correction is detected from a difference between the item image data and reference image data. By setting to be a reference range an area wider than an area where the basic medical information is arranged (an area indicated by the print area information), the presence or absence of the correction is more reliably detected.

The image generator 20 generates the reference image data corresponding to the basic medical information based on the encoded information represented in the medical record sheet image data. The image generator 20 includes a decoding processor 22 and an image reproducer 24. The functions of the decoding processor 22 and the image reproducer 24 are described below.

The decoding processor 22 decodes the encoded information represented in the medical record sheet image data in accordance with a preset decoding condition. The decoded basic medical information is thus generated. If the encoded information is generated by encoding the basic medical information, the decoded basic medical information is identical in content to the basic medical information.

In accordance with a preset reproduction condition, the image reproducer 24 reproduces the reference image data representing the basic medical information from the decoded basic medical information generated by the decoding processor 22. The reproduction condition is identical to the print expression condition described above. For example, as the print expression condition, the reproduction condition includes the order of the print location of each item of the basic medical information, the layout of the print location, the type of a font of the character string, the size of the font, and the positional relationship of the character strings. The contents of the condition are identical to those of the print expression condition. More specifically, the image reproducer 24 reproduces the reference image data from the decoded basic medical information in accordance with a condition similar to the print expression condition of the basic medical information. In this way, each item of the basic medical information is expressed in the reference image data under the condition similar to the print expression condition. The reference image data is output to the correction detector 28. If the print expression condition is different depending on the type of the medical record sheet, the image reproducer 24 reproduces the reference image data in accordance with the reproduction condition corresponding to the type of the medical record sheet. The image reproducer 24 may reproduce item reference image data representing each individual item of the basic medical information.

The reproduction condition memory 26 pre-stores reproduction condition information indicating a reproduction condition. For example, the reproduction condition memory 26 stores the reproduction condition information of each type of medical record sheet. The reproduction condition memory 26 may also store the reproduction condition information indicating the reproduction condition of an individual item. The image reproducer 24 reproduces the reference image data in accordance with the reproduction condition information stored on the reproduction condition memory 26.

The reproduction condition memory 26 may not be necessarily included in the image processing apparatus 10. For example, the server 50 may store the reproduction condition information. In such a case, the image reproducer 24 retrieves the reproduction condition information from the server 50 and then reproduces the reference image data. The reproduction condition information may encoded together with the basic medical information and included in the encoded information. In such a case, the image reproducer 24 reproduces the reference image data in accordance with the reproduction condition information generated by decoding the encoded information.

The correction detector 28 detects a correction on the basic medical information printed on the medical record sheet by extracting a difference between the basic medical information image data and the reference image data. The correction detector 28 may also detect a correction by extracting a difference between the item image data and the item reference image data. The correction detector 28 outputs detection results to the controller 30. The correction to the basic medical information may be an addition, a hand-written correction, a post-process, or the like.

The controller 30 controls the elements of the image processing apparatus 10. In the present embodiment, the controller 30 performs a process responsive to the detection results of the correction detector 28. If no correction is detected by the correction detector 28, the controller 30 outputs to the transceiver 32 the medical record sheet image data generated by the image reader 12. The controller 30 then attaches to the medical record sheet image data the decoded basic medical information generated by decoding the encoded information. If a correction is detected by the correction detector 28, the controller 30 causes the display 34 to display warning information indicating that the basic medical information has been corrected. Also, if the correction is detected by the correction detector 28, the controller 30 may enter a correction mode to correct the decoded basic medical information. When the decoded basic medical information is corrected in the correction mode, the controller 30 attaches the corrected decoded basic medical information to the medical record sheet image data, and then outputs the resulting medical record sheet image data to the transceiver 32. The controller 30 may cause the display 34 to display the medical record sheet image data or may cause the display 34 to display difference image data representing the difference between the basic medical information image data and the reference image data.

The transceiver 32 is a network interface, and transmits and receives data via the communication network N. In the present embodiment, the transceiver 32 transmits the medical record sheet image data to the server 50. In this way, the server 50 stores the medical record sheet image data on a preset storage location.

The controller 30 is connected to an operation unit 36. The operation unit 36 may include a keyboard or a touchpanel. The user may correct the decoded basic medical information using the operation unit 36.

The server 50 stores the medical record sheet image data transmitted from the image processing apparatus 10. In the present embodiment, the medical record sheet image data is managed in accordance with the decoded basic medical information attached to the medical record sheet image data. For example, the server 50 produces a folder on a per patient basis in accordance with a patient ID, and the medical record sheet image data is stored in the folder. A folder may be produced on a per service basis or on a per examination date basis, and the medical record sheet image data may be stored in the folder thus produced.

The image processing apparatus 10 may be implemented by a hardware resource operating in cooperation with software. More specifically, the image processing apparatus 10 includes a processor, such as a central processing unit (CPU) (not illustrated). The processor reads a program stored on a storage device (not illustrated), and executes the program. The function of the image processor 14 and the controller 30 is thus implemented. The program is stored on the storage device through a storage medium, such as a compact disk (CD) or a digital versatile disk (DVD), or a communication network.

FIG. 2 illustrates a specific example of a medical record sheet 100. The medical record sheet 100 is an original document, and may be a medical chart sheet or a medical interview sheet for use in a medical institution, such as a hospital. Pre-printed on the medical record sheet 100 are basic medical information 102 and a two-dimensional barcode 104. The basic medical information 102 includes items, such as a patient ID, a patient name, a medical service, a document type, and a date of examination. In the example of FIG. 2, character strings "patient ID: 00001", "patient name: Taro FUJI", "service: internal medicine", "document type: patient referral document", and "examination date: 2013/11/08" are printed on a preset print area on the medical record sheet 100. The two-dimensional barcode 104 is an example of the encoded information. The two-dimensional barcode 104 is generated by encoding information of the items (the patient ID, the patient name, the service, the type of document, and the examination date) included in the basic medical information 102. The encoded information may not be limited to the two-dimensional barcode 104. The encoded information may be a one-dimensional barcode, or information encoded in a different format. The two-dimensional barcode 104 is printed on the medical record sheet 100 in a visible state. The encoded information of the present embodiment may be printed on the medical record sheet 100 in an invisible state. Information indicating a storage location of the medical record sheet image data may be encoded together with the basic medical information 102 and included in the two-dimensional barcode 104.

As illustrated in FIG. 2, the examination date of the basic medical information 102 is corrected as indicated by a correction location 106. More specifically, double lines are drawn across the character string "08" as the "day" portion of the examination date (2013/11/08), and correction characters "09" are hand-written next to the crossed character string "08". Such a correction may be made by an authorized person, such as a doctor.

A correction to the basic medical information 102 may be made in a variety of situations. For example, the basic medical information 102 may be corrected in home health care. In the home health care field, a doctor may visit the home of a patient for medical service and may write the performed medical service on the medical record sheet 100. A doctor may visit homes of multiple patients. Generally, the medical record sheet 100 is not printed at the home of a patient but the medical record sheet 100 of the patient expected to receive a doctor's visit that day is typically printed at the doctor's hospital or clinic. If a doctor is obliged to examine in a hurry a patient who is not scheduled to receive the doctor's visit, the doctor may have no medical record sheet 100 of that patient at hand. The doctor then may modify the medical record sheet 100 of another patient for temporary use. Also, the doctor may modify the medical record sheet 100 of one patient whose schedule is canceled and use the modified medical record sheet 100 for another patient. In this way, the medical record sheet 100 of one patient may be intentionally used for another patient. In such a case, the printed basic medical information 102 may be hand-written corrected in accordance with the visited patient, the examination date, and the medical service. The printed basic medical information 102 is thus corrected, but the correction is not reflected in the two-dimensional barcode 104.

FIG. 3 illustrates an example of a print area management table. The print area information is prepared for each type of the medical record sheet 100 (on a per sheet ID basis), and is thus managed by the print area management table of FIG. 3. The sheet ID in the print area management table indicates information of the type of the medical record sheet 100. The print area management table is pre-stored on the print area memory 18. The print area may be a rectangular area, for example. If the top left corner of the medical record sheet 100 is the origin (0,0), the print area is defined by coordinates of a start point (top left corner) and coordinates of an end point (bottom right corner). The image extractor 16 identifies the print area from the print area management table in accordance with the sheet ID of the medical record sheet 100. The image extractor 16 extracts, from the medical record sheet image data, the basic medical information image data representing a portion corresponding to the print area. The sheet ID may be encoded together with the basic medical information and included in the two-dimensional barcode 104. The sheet ID is then obtained by decoding the two-dimensional barcode 104, and the image extractor 16 identifies the print area using the decoded sheet ID. The print area management table may be stored on the server 50. In such a case, the image extractor 16 retrieves the print area information corresponding to the sheet ID from the server 50 to identify the print area.

Regardless of the type of the medical record sheet 100, the basic medical information 102 may be printed on a preset location in the medical record sheet 100. In such a case, the image extractor 16 extracts, from the medical record sheet image data, image data of a portion at the preset location as the basic medical information image data. The print area management table is not involved.

The print area memory 18 may pre-store the print area management table indicating the print area in a per item basis of the basic medical information 102. FIG. 4 illustrates an example of the print area management table of each item. For example, the print areas are respectively set up for the "patient ID", the "patient name", the "service", the "document type", and the "examination date". Each item may be divided into sub-items. For example, the "examination date" may be divided into sub items of the "year", the "month", and the "day", and print areas are respectively set up for these sub-items. The "patient name" may be divided into sub-items respectively for the "family name" and the "given name", and print areas are respectively set up for these sub-items. By referencing the print area management table, the image extractor 16 identifies the print area of each item. The image extractor 16 individually extracts from the medical record sheet image data the item image data of each of the individual items.

Figure 5:
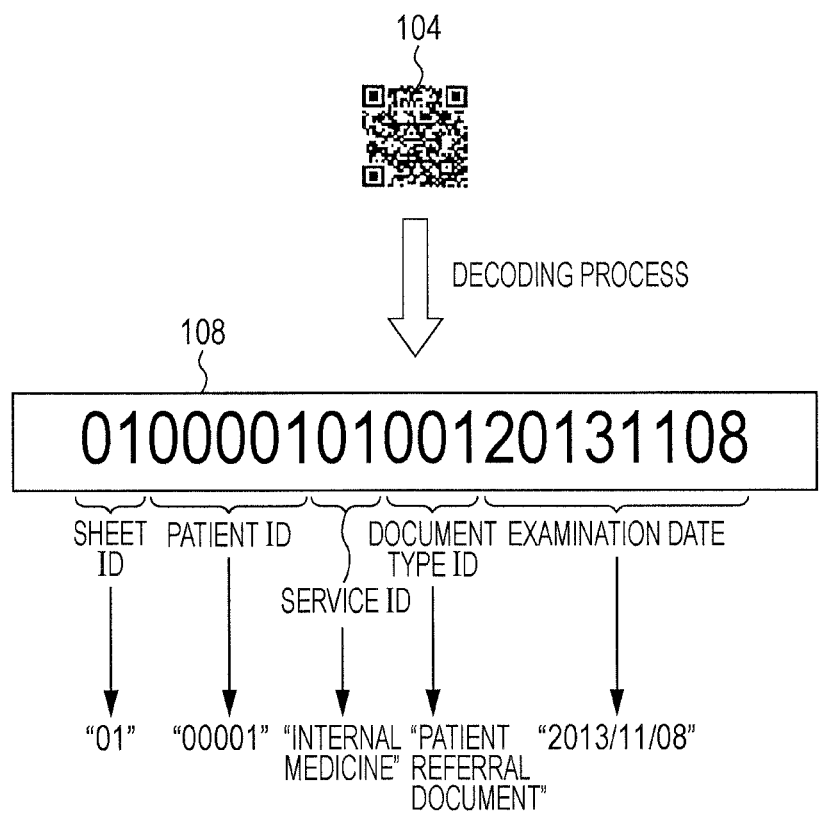
FIG. 5 illustrates an example of decoded information.

FIG. 5 illustrates an example of the decoded basic medical information (decoded information). When the two-dimensional barcode 104 is decoded by the decoding processor 22, decoded basic medical information 108 corresponding to the basic medical information 102 is generated. The decoded basic medical information 108 includes a string of numbers and characters in accordance with a preset rule. Numerals included in the decoded basic medical information 108 correspond to information of each item of the basic medical information 102. As illustrated in FIG. 5, leading numbers "01" indicate the sheet ID, the next numbers "00001" indicate a patient ID, the next numbers "01" indicate a service ID, the next numbers "001" indicate a document type ID, and the last numbers "20131108" indicate an examination date. Since the two-dimensional barcode 104 is an encoded form of the basic medical information 102, each item of the decoded basic medical information 108 is identical in content to the corresponding item of the basic medical information 102. More specifically, the patient ID "00001" in the decoded basic medical information 108 is identical to the patient ID in the basic medical information 102. The service indicated by the service ID "01" is the medical service "internal medicine" in the basic medical information 102. The document type ID "001" is identical to the document type "patient referral document" in the basic medical information 102. The examination date "20131108" indicates that the examination date is "2013/11/08", and is thus the same as the examination date in the basic medical information 102. The decoded basic medical information 108 is output to the image reproducer 24.

The image reproducer 24 reproduces the reference image data representing the basic medical information 102 based on each piece of information included in the decoded basic medical information 108. For example, the reproduction condition memory 26 pre-stores patient name information indicating the patient name identified by a patient ID, service information indicating a medical service identified by a service ID, document type information indicating a document type identified by a document type ID, and format information indicating the format of date. The image reproducer 24 retrieves from the reproduction condition memory 26 the patient name information identified by the patient ID included in the decoded basic medical information 108, the service information identified by the service ID, the document type information identified by the document type ID, and the format information included in the decoded basic medical information 108. In accordance with the format information, the image reproducer 24 converts the information of the examination date "20131108" into information represented by the date format "2013/11/08". The patient name information, the service information, the document type information, and the format information may be stored on an external apparatus, such as the server 50. In such a case, the image reproducer 24 retrieves the patient name information and the other information from the external apparatus.

Based on the contents of the items (the patient ID, the patient name, the medical service, the document type, and the examination date) acquired from the decoded basic medical information 108, the image reproducer 24 reproduces the reference image data in the expression format similar to the printed basic medical information 102 in accordance with the reproduction condition. In the present embodiment, the image reproducer 24 generates the reference image data representing the basic medical information 102 in a fashion similar to the print expression condition of the basic medical information 102 (under the condition similar to the print expression condition). Printed as the basic medical information 102 are the order and layout of the locations of the character strings, the type of the font, the font size, and the positional relationship of the characters of each item acquired from the decoded basic medical information 108. In this way, the contents of the items ("patient ID: 00001", "patient name: Taro FUJI", "service: internal medicine", "document type: patient referral document", and "examination date: 2013/11/08") are displayed generally under the condition similar to the print expression condition. More specifically, the image reproducer 24 images each piece of information from the decoded basic medical information 108 in accordance with an expression format similar to the printed basic medical information 102, and thereby reproduces the reference image data identical to the basic medical information 102. The reference image data serves as basic data in an detection operation, in which the presence of a correction is detected from a difference between the item image data and the reference image data. By setting to be a reference range an area wider than an area where the basic medical information is arranged, the presence or absence of the correction is more reliably detected.

Figure 6:
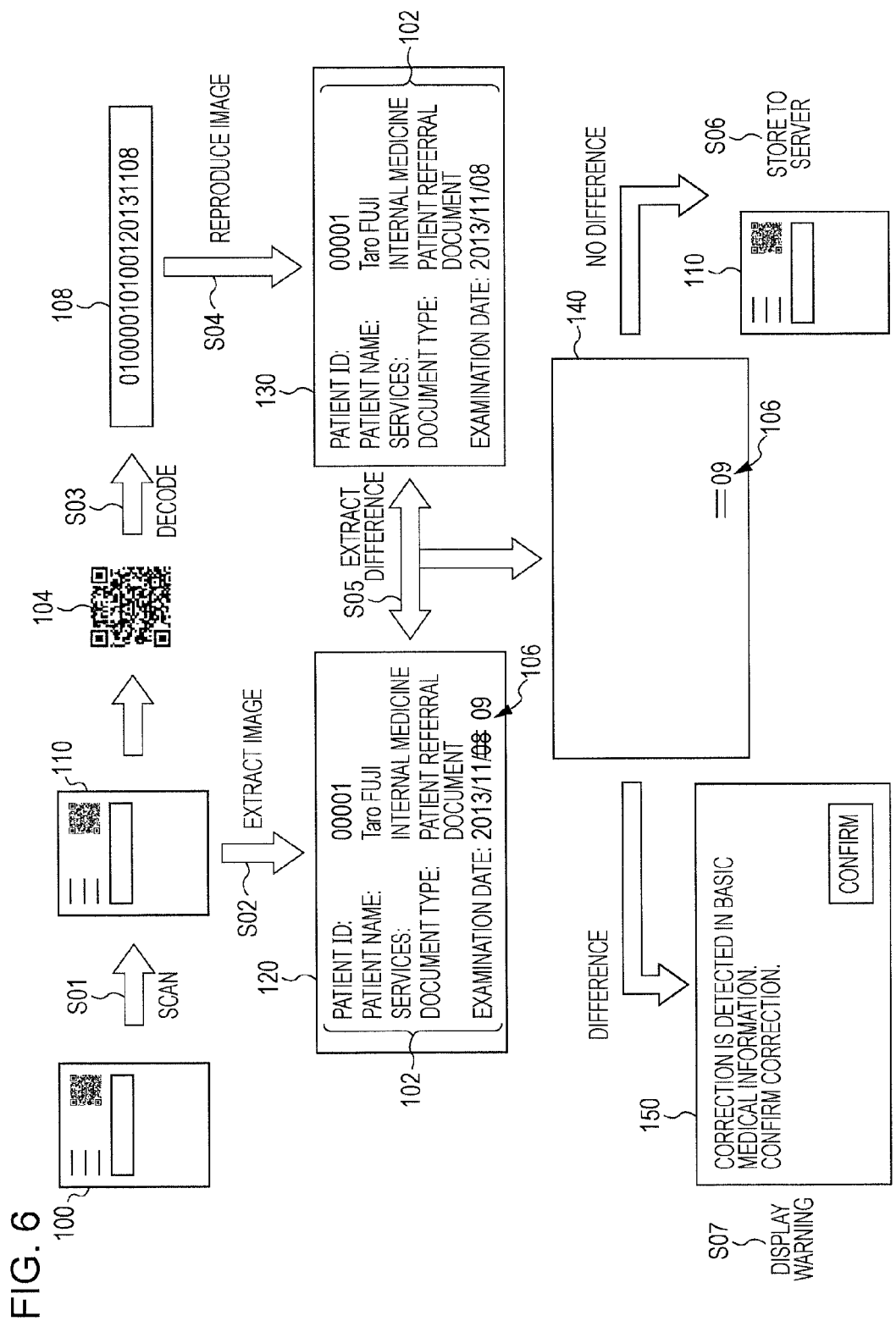
FIG. 6 illustrates an example of a correction detection process.

Referring to FIG. 6, the operation of the image processing apparatus 10 is described below. When the user uses the operation unit 36 to instruct the medical record sheet 100 to be scanned, the image reader 12 reads an image on the medical record sheet 100 (S01). Medical record sheet image data 110 representing the medical record sheet 100 is thus generated. As illustrated in FIG. 2, the portion of "day" in the examination date is hand-written corrected from "08" to "09" in the basic medical information 102, and that correction portion 106 is also expressed in the medical record sheet image data 110.

The image extractor 16 retrieves the print area information from the print area memory 18 and extracts, from the medical record sheet image data 110, basic medical information image data 120 representing a portion corresponding to the print area (S02). The basic medical information 102 and the correction location 106 are represented in the basic medical information image data 120. The image extractor 16 may binarize the basic medical information image data 120. The decoding processor 22 decodes the two-dimensional barcode 104 represented in the medical record sheet image data 110 (S03). The decoded basic medical information 108 corresponding to the basic medical information 102 is thus generated. The image reproducer 24 retrieves the reproduction condition information from the reproduction condition memory 26, and reproduces reference image data 130 from the decoded basic medical information 108 in accordance with the reproduction condition (S04). The reproduction condition is identical to the print expression condition in the printing operation of the basic medical information 102. In the reference image data 130, the same content as the printed basic medical information 102 is expressed in the same format as the basic medical information 102. Since the correction location 106 in the medical record sheet 100 is not reflected in the two-dimensional barcode 104, the reference image data 130 does not include the correction location 106. The order of the extraction operation in S02 and the image reproduction operation in S03 and S04 is not limited to the order described above. The image reproduction operation may be performed prior to the extraction operation. The extraction operation and the image reproduction operation may be concurrently performed.

The correction detector 28 extracts the difference between the basic medical information image data 120 and the reference image data 130 (S05). Difference image data 140 is thus generated. The correction location 106 is reflected in the basic medical information image data 120 while the correction location 106 is not reflected in the reference image data 130. The difference thus corresponds to the correction location 106.

If no difference is detected, the controller 30 attaches to the medical record sheet image data 110 the basic medical information decoded from the two-dimensional barcode 104, and outputs the resulting medical record sheet image data 110 to the transceiver 32. The transceiver 32 transmits the medical record sheet image data 110 to the server 50. In this way, the medical record sheet image data 110 is stored on the server 50 (S06). The server 50 manages the medical record sheet image data 110 in accordance with the decoded basic medical information attached to the medical record sheet image data 110.

If the difference is detected on the other hand, the controller 30 causes the display 34 to display a warning 150 (S07). In such a case, the medical record sheet image data 110 is not transmitted to the server 50. Optionally, the controller 30 may cause the display 34 to display the medical record sheet image data 110.

If the difference is detected in this way, the controller 30 may correct the decoded basic medical information in the correction mode. During the correction mode, the user corrects the decoded basic medical information using the operation unit 36. In the example of FIG. 6, the portion of "day" of the examination date is hand-written corrected from "08" to "09" in the medical record sheet 100. If the user corrects the portion of the "day" in the examination date from "08" to "09" using the operation unit 36, the controller 30 corrects the portion of the "day" of the examination date indicated by the decoded basic medical information from "08" to "09". In this way, the correction by the user is reflected in the decoded basic medical information. The controller 30 attaches the decoded basic medical information subsequent to the correction to the medical record sheet image data 110. If the user instructs the medical record sheet image data 110 to be transmitted using the operation unit 36, the medical record sheet image data 110 is transmitted to the server 50 via the transceiver 32 and the communication network N. The server 50 manages the medical record sheet image data 110 in accordance with the decoded basic medical information subsequent to the correction. In this case, the medical record sheet image data 110 is managed in accordance with the corrected examination date "2013/11/9".

Extracted in the present embodiment is the difference between the basic medical information image data 120 extracted from the medical record sheet image data 110 and the reference image data 130 reproduced from the two-dimensional barcode 104. The basic medical information image data 120 represents the basic medical information 102 subsequent to the correction. The reference image data 130 represents the basic medical information 102 prior to the correction. The correction to the basic medical information 102 printed on the medical record sheet 100 is thus detected by extracting the difference between the basic medical information image data 120 and the reference image data 130. Since the reference image data 130 is reproduced under the same reproduction condition as the print expression condition of the basic medical information 102 in the present embodiment, the comparison of the images leads to the extraction of the difference and thus the detection of the correction. The correction is detected without using an optical character recognition (OCR) process. Since the correction is detected through the comparison of the images in the present embodiment, the correction is detected even if reading is difficult through the OCR process.

When the correction is detected in the present embodiment, the medical record sheet image data 110 is not transmitted to the server 50. The server 50 is free from managing the medical record sheet image data 110 based on the basic medical information prior to the correction.

Since the correction is detected by the image processing apparatus 10 in the present embodiment, the user is free from a manual detection operation of correction. If the manual detection operation of correction is performed, the user has to visually check the presence or absence of a correction by causing the display 34 to display the medical record sheet image data 110 each time the image of the medical record sheet 100 is read. For example, multiple images (for example, as many as 100 images) of the medical record sheet 100 are read, the user visually checks the presence or absence of a correction on the images one by one. This job is greatly time-consuming. There is also a possibility of an operation error in visual checking. For example, the user may fail to notice a correction. Since the image processing apparatus 10 automatically detects a correction in the present embodiment, time to check the correction is saved, and the possibility of the operation error by the user may be reduced.

Figure 7:
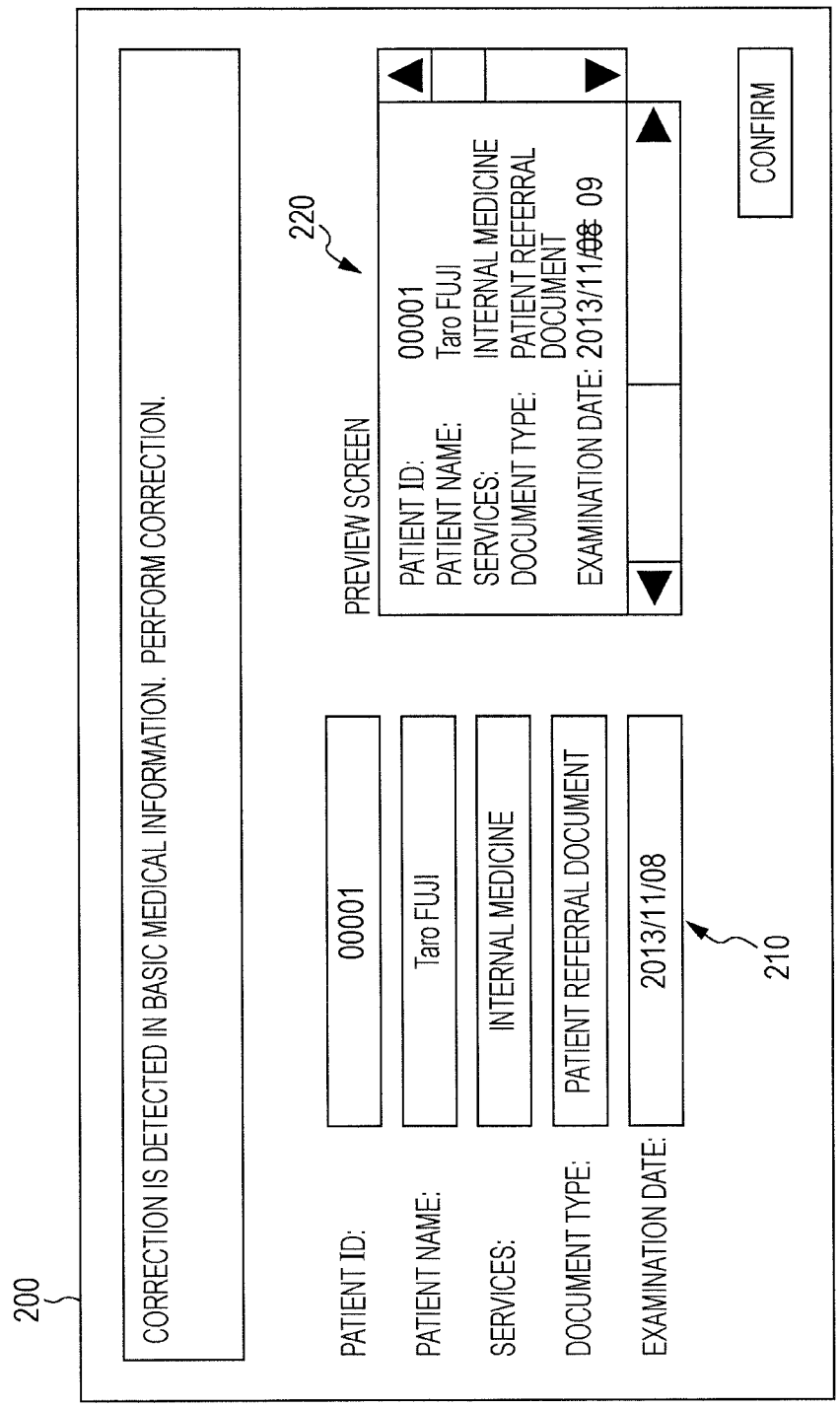
FIG. 7 illustrates an example of a screen to modify the basic medical information.

A specific example of the correction mode is described with reference to FIG. 7. If a correction is detected by the correction detector 28, the controller 30 enters the operation mode. For example, if a difference is extracted as a result of the comparison of the basic medical information image data 120 with the reference image data 130 in the whole basic medical information 102, the controller 30 causes the display 34 to display a correction screen 200. An amount of image data representing the difference (such as the number of difference pixels) is compared with a preset threshold value. If the amount of image data representing the difference is above the threshold value, the difference may be treated as being caused by a correction. This method excludes a smear on the medical record sheet or the like, not caused by a correction, and increases the correction detection accuracy. The correction screen 200 includes a correction column 210 where each item of the basic medical information is to be corrected, and a preview screen 220. If a difference is detected with the whole basic medical information 102 as a target, it is not identified which item of the basic medical information 102 has been corrected. In such a case, all the items of the information are permitted to be corrected. In the example of FIG. 7, the items of the patient ID, the patient name, the service, the document type, and the examination date are permitted to be corrected.

The controller 30 causes the decoded basic medical information obtained by decoding the two-dimensional barcode 104 to be displayed in the correction column 210 as default information of each item. The controller 30 causes an area having the basic medical information 102 in the medical record sheet image data 110 to be displayed in the preview screen 220. The user scrolls the image displayed on the preview screen 220 using the operation unit 36. In this way, a peripheral area of the basic medical information 102 is displayed on the preview screen 220. The user may verify the correction content on the basic medical information 102 by referencing the basic medical information 102 and the peripheral area thereof displayed in the preview screen 220.

The user may correct the content of an item as a correction target in the correction column 210 by using the operation unit 36. The following correction methods may be available. For example, a text box is displayed to prompt the user to enter a correction character, or a drop-down list of correction candidates is displayed to prompt the user to select a correction character from the candidates. If a correction to the item "patient name" is detected, the user desirably corrects the item "patient ID" as well. Similarly, if a correction to the item "patient ID" is detected, the user desirably corrects the item "patient name" as well.

If a confirm button is selected by the user with the decoded basic medical information corrected, the correction mode ends. The controller 30 attaches the corrected decoded basic medical information to the medical record sheet image data 110 and outputs the resulting medical record sheet image data 110 to the transceiver 32. In this way, the transceiver 32 transmits to the server 50 the medical record sheet image data 110 with the corrected decoded basic medical information attached thereto. The server 50 manages the medical record sheet image data 110 in accordance with the corrected decoded basic medical information.

Referring to FIG. 8, another example of the correction mode is described. The correction detector 28 compares the item image data with the item reference image data, and detects a correction on a per item basis. The controller 30 permits a correction on an item detected by the correction detector 28 to be performed, and inhibits a correction on an item from which no correction is detected. More specifically, the controller 30 causes each item of the decoded basic medical information as default information in a correction column 212. For example, if there is a correction on the portion of the item "examination date" of the basic medical information 102, the controller 30 permits a correction to be performed on the item "examination date", and inhibits a correction on the other items. Since no correction is detected in the shadowed items (the patient ID, the patient name, the service, and the document type) in the correction column 212, the correction is inhibited in these items. If the confirm button is selected by the user with the correction made, the medical record sheet image data 110 with the corrected decoded basic medical information attached thereto is transmitted to and imaged by the server 50. In this way, an item having no correction detected is free from an erratic modification. If the correction detector 28 detects a correction in the item "patient name" or the item "patient ID", the controller 30 permits a correction on both the item "patient name" and the item "patient ID".

If the correction detector 28 detects a correction in a sub-item, a correction may be permitted on that sub-item, and inhibited on the other items and sub-items. More specifically, as illustrated in FIG. 9, the controller 30 causes each item of the decoded basic medical information as default information in a correction column 214. For example, if a correction is detected in the portion of the sub-item "day" of the item "examination date" of the basic medical information 102, the controller 30 permits a correction in the sub-item "day", and inhibits correction in the other items and sub-items. Since no correction is detected in the shadowed items (the patient ID, the patient name, the service, the document type, the year and month of the examination date) in the correction column 214, the correction is inhibited in these items. If the user selects the confirm button with the correction made, the medical record sheet image data 110 with the corrected decoded basic medical information attached thereto is transmitted to and managed by the server 50. In this correction mode, an item or a sub-item having no correction detected is free from an erratic modification. Optionally, an item from which the correction detector 28 has detected a correction may be changed by the user. For example, the correction detector 28 may detect a correction in the "document type", but, it is in fact found that a preview screen indicates that the "examination date" has been corrected. In such a case, a "modify correction item" button may be arranged on a correction screen 200. Each time the button is clicked (selected), the correction item is changed one by one. The erratic detection of the correction detector 28 is thus corrected.

First Modification

Figure 10:
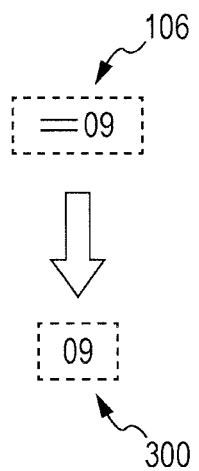
FIG. 10 illustrates a process of a first modification.

A first modification of the embodiment is described below with reference to FIG. 10. In the first modification, a hand-written corrected character string is optical character recognition (OCR) processed, and a correction candidate is identified by the OCR results. The first modification is described in detail below.

In response to the location of the difference extracted by the correction detector 28, the controller 30 identifies the correction location 106 that is hand-written corrected. As illustrated in FIG. 10, for example, the correction location 106 includes a region where a correction mark indicating a correction (double lines) is drawn, and a region where a correction character (09) is written. The correction mark typically overwrites a correction target of the basic medical information 102 printed on the medical record sheet 100. The region having the correction mark written thereon is thus identified using the print area information of the basic medical information 102. Based on the print area information of the basic medical information 102, the controller 30 identifies the region where the correction mark is written. The controller 30 removes the portion of the correction mark (the portion of the basic medical information 102) from the correction location 106, and performs the OCR process on a region 300 with the portion of the correction mark removed. The OCR process is performed with the correction mark (double lines) removed, and the correction character "09" is identified. During the correction mode, the controller 30 causes the correction character "09" as a correction candidate to be displayed in the correction screen. For example, the controller 30 may display a list including the correction character "09" and other correction candidates. The controller 30 may display the correction character "09" in a text box as a default value. Since a corrected character is displayed as a correction candidate in the first modification, the correction accuracy of the decoded basic medical information is increased. The selection of the correction candidate is efficiently performed.

Second Modification

Figure 11:
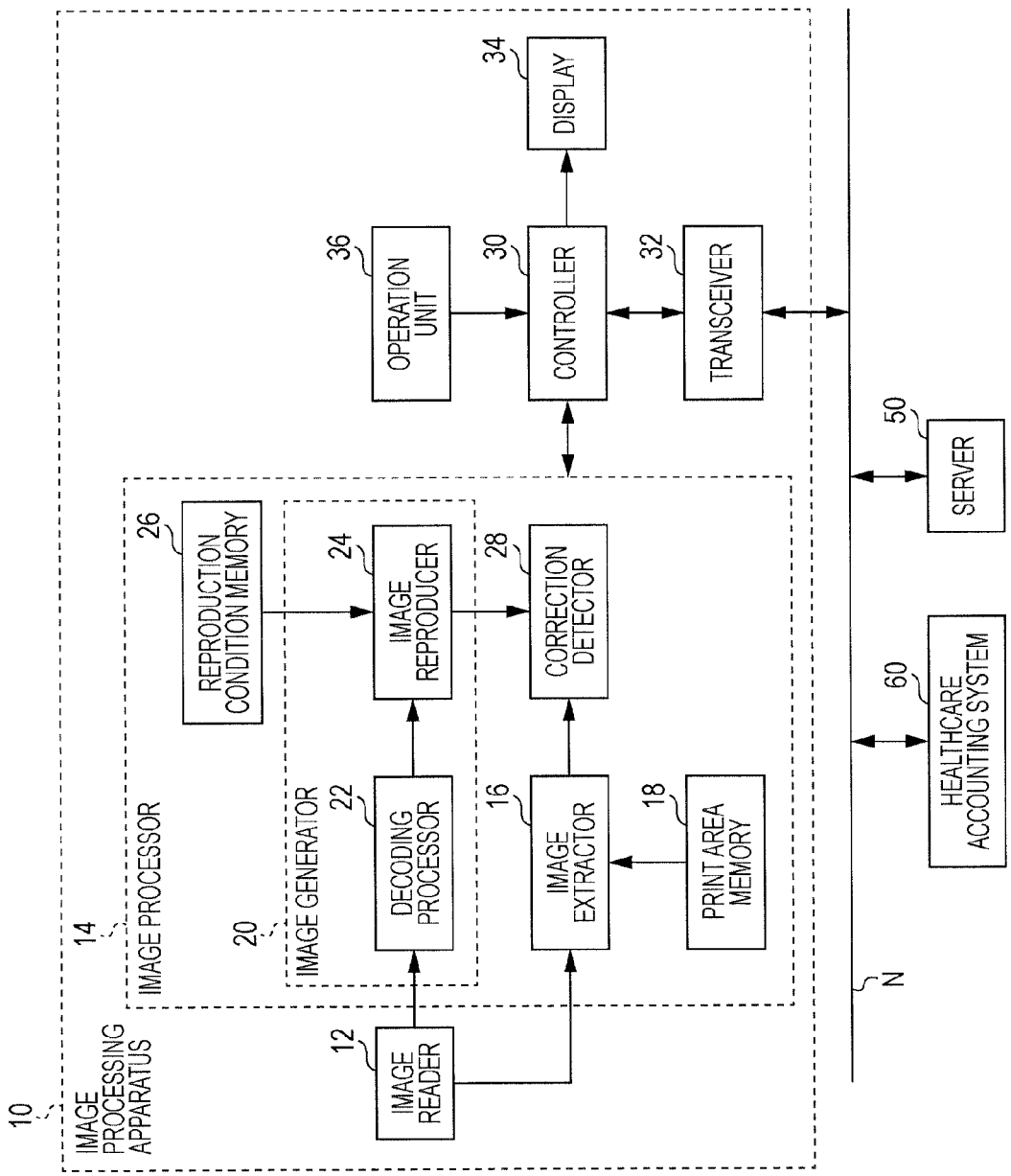
FIG. 11 is a block diagram illustrating an example of a system of a second modification.
Figure 12:
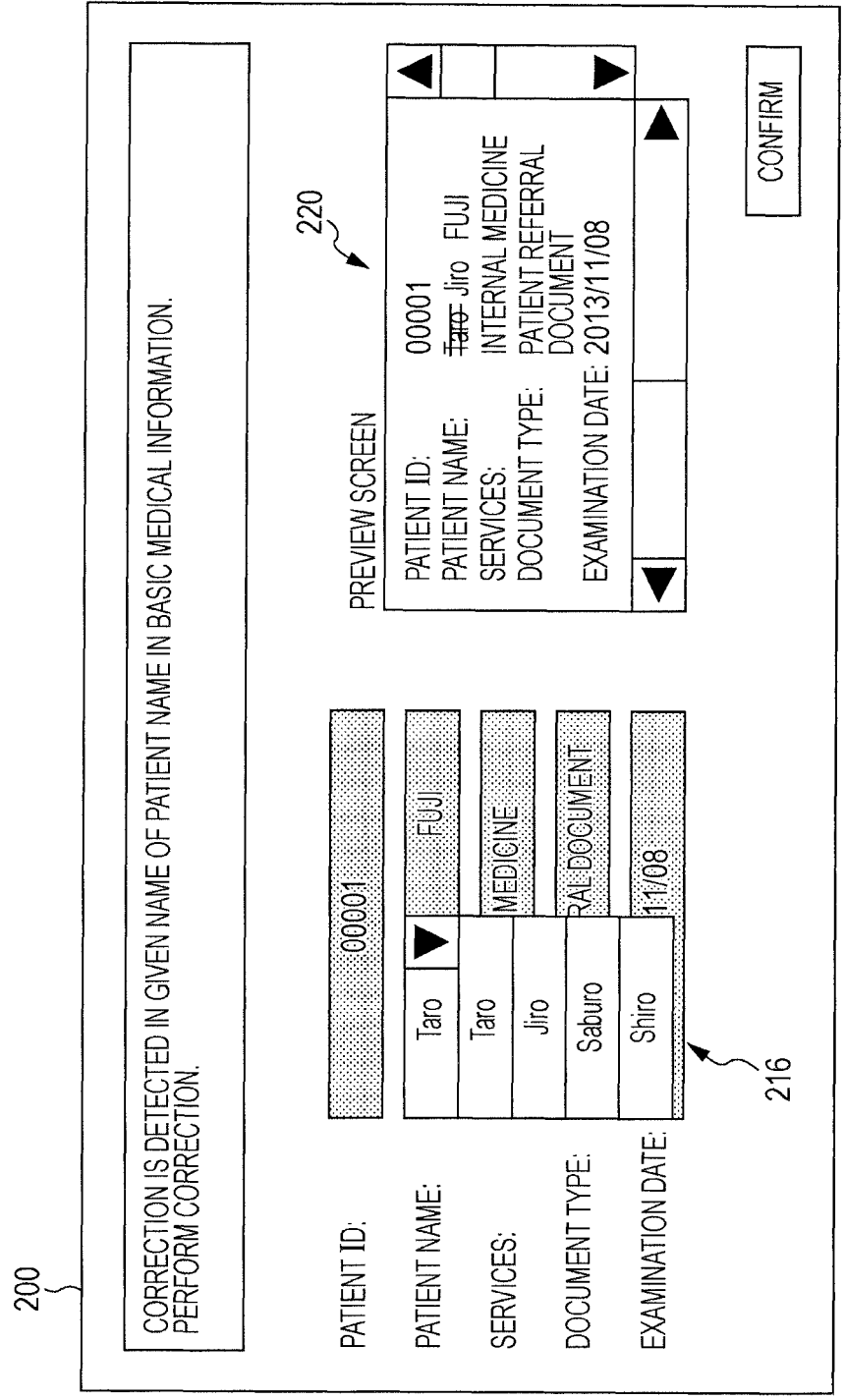
FIG. 12 illustrates an example of the screen to modify the basic medical information.

A second modification of the embodiment is described with reference to FIG. 11 and FIG. 12. FIG. 11 is a block diagram illustrating an example of a system of the second modification. In the second modification, a healthcare accounting system 60 is connected to the communication network N. The healthcare accounting system 60 is used by a medical institution to perform patient accepting and clinical fee accounting. The healthcare accounting system 60 stores, in an associated form, patient information (a patient ID and a patient name) identifying the patient, accepting and accounting information related to accepting the patient and settlement of the patient's clinical fees, and diagnosis history information related to past medical care. The accepting and accounting information indicates a reception state of a patient to a medical institution (as to whether an accepting process is under way or not), a reservation state of the patient to medical care in the medical institution (the presence or absence of the patient's reservation), a state of the fee settlement of the patient to the medical institution (as to whether the clinical fees are settled or not). The image processing apparatus 10 is connected to the healthcare accounting system 60 via the communication network N.

During the second modification, the controller 30 retrieves, from the healthcare accounting system 60, information related to an item from which the correction detector 28 has detected a correction and then displays the information as a correction candidate in the correction mode.

More specifically, if the correction detector 28 detects a correction in the portion of the item "patient name" by comparing the item image data with the item reference image data, the controller 30 performs the following operation. The controller 30 retrieves the patient information of a patient having settled the clinical fees from the healthcare accounting system 60 on the same day as the "examination date" indicated by the decoded basic medical information. The controller 30 displays a list of the patient names indicated by the patient information as candidates in the column of the item "patient name" in the correction column. Since the "examination date" of the basic medical information 102 is not corrected, the names of patients who have received medical care on the same examination day are displayed as correction candidates. The selection of the correction candidate is thus efficiently performed.

If the correction detector 28 detects a correction in the portion of the sub-item "given name" of the patient name, the controller 30 performs the following operation. The controller 30 retrieves from the healthcare accounting system 60 the patient information of the same "family name" as the "family name" indicated by the decoded basic medical information. As illustrated in FIG. 12, the controller 30 displays a list of "given names" indicated by the patient information as the candidates 216. The user selects a corrected "given name" from the candidates 216 displayed in a list using the operation unit 36. In the basic medical information 102, the "given name" is corrected, and the "family name" is not corrected. The patients having the same "family name" are displayed as correction candidates. The correction candidate is thus efficiently selected.

If the correction detector 28 detects a correction in the portion of the item "examination date", the controller 30 performs the following operation. The controller 30 retrieves, from the healthcare accounting system 60, the diagnosis history information indicating the nearest preceding medical care day of the patient name indicated by the decoded basic medical information. The controller 30 displays a list of examination days indicated by the diagnosis history information in the column of the item "examination date" of the correction screen. Since neither "patient name" nor "patient ID" in the basic medical information 102 is corrected, the examination day of that patient is displayed as a correction candidate. The correction candidate is efficiently selected.

The foregoing description of the exemplary embodiments of the present invention has been provided for the purposes of illustration and description. It is not intended to be exhaustive or to limit the invention to the precise forms disclosed. Obviously, many corrections and variations will be apparent to practitioners skilled in the art. The embodiments were chosen and described in order to best explain the principles of the invention and its practical applications, thereby enabling others skilled in the art to understand the invention for various embodiments and with the various corrections as are suited to the particular use contemplated. It is intended that the scope of the invention be defined by the following claims and their equivalents.

What is claimed is:

1. An image processing apparatus comprising:
   a processor configured to execute;
   an extractor configured to receive sheet image data that is generated by reading an image on a medical record sheet onto which basic medical information and encoded information representing the basic medical information are printed, and extract, from the sheet image data, information image data representing a portion where the basic medical information is printed;
   an image generator configured to generate reference image data representing the basic medical information, based on the encoded information represented in the sheet image data;
   a detector configured to detect a correction that is to be performed on the basic medical information printed on the medical record sheet, based on a difference between the information image data and the reference image data;
   a decoding unit configured to generate decoded information by decoding the encoded information; and
   an image reproducing unit configured to reproduce the reference image data from the decoded information in accordance with an expression condition to be used for comparison with the information image data.

2. The image processing apparatus according to claim 1, wherein the image reproducing unit is configured to reproduce the reference image data from the decoded information in accordance with an expression condition similar to an expression condition for the basic medical information printed on the medical record sheet.

3. The image processing apparatus according to claim 1, wherein the basic medical information comprises a plurality of items,
   wherein the extractor is configured to extract the information image data on a per item basis,
   wherein the image reproducing unit is configured to reproduce the reference image data on a per item basis, and
   wherein the detector is configured to detect the correction on a per item basis.

4. The image processing apparatus according to claim 2, wherein the basic medical information comprises a plurality of items,
   wherein the extractor is configured to extract the information image data on a per item basis,
   wherein the image reproducing unit is configured to reproduce the reference image data on a per item basis, and
   wherein the detector is configured to detect the correction on a per item basis.

5. The image processing apparatus according to claim 1, wherein the processor is further configured to execute an executing unit configured to execute an operation related to the correction on the decoded information if the detector has detected the correction.

6. The image processing apparatus according to claim 2, wherein the processor is further configured to execute an executing unit configured to execute an operation related to the correction on the decoded information if the detector has detected the correction.

7. The image processing apparatus according to claim 3, wherein the processor is further configured to execute an executing unit configured to execute an operation related to the correction on the decoded information if the detector has detected the correction.

8. The image processing apparatus according to claim 4, wherein the processor is further configured to execute an executing unit configured to execute an operation related to the correction on the decoded information if the detector has detected the correction.

9. The image processing apparatus according to claim 5, wherein the execution unit is configured to execute an operation related to the correction of a portion corresponding to a difference between the information image data and the reference image data in the decoded information.

10. The image processing apparatus according to claim 6, wherein the execution unit is configured to execute an operation related to the correction of a portion corresponding to a difference between the information image data and the reference image data in the decoded information.

11. The image processing apparatus according to claim 7, wherein the execution unit is configured to execute an operation related to the correction of a portion corresponding to a difference between the information image data and the reference image data in the decoded information.

12. The image processing apparatus according to claim 8, wherein the execution unit is configured to execute an operation related to the correction of a portion corresponding to a difference between the information image data and the reference image data in the decoded information.

13. The image processing apparatus according to claim 9, wherein the execution unit is configured to output information indicating a correction candidate to the portion corresponding to the difference.

14. The image processing apparatus according to claim 10, wherein the execution unit is configured to output information indicating a correction candidate to the portion corresponding to the difference.

15. The image processing apparatus according to claim 13, wherein the execution unit is configured to identify a character to be modified from the portion corresponding to the difference and outputs, as the correction candidate, information indicating the character to be modified.

16. The image processing apparatus according to claim 14, wherein the execution unit is configured to identify a character to be modified from the portion corresponding to the difference and outputs, as the correction candidate, information indicating the character to be modified.

17. The image processing apparatus according to claim 1, wherein the processor is further configure to execute an output unit configured to output a warning if the detector detects the correction.

18. An image processing method of a processor of a processing apparatus, the method comprising,
receiving sheet image data that is generated by reading an image on a medical record sheet onto which basic medical information and encoded information representing the basic medical information are printed, and extracting, from the sheet image data, information image data representing a portion where the basic medical information is printed;
generating reference image data representing the basic medical information, based on the encoded information represented in the sheet image data;
detecting a correction that is to be performed on the basic medical information printed on the medical record sheet, based on a difference between the information image data and the reference image data;
generating decoded information by decoding the encoded information; and
reproducing the reference image data from the decoded information in accordance with an expression condition to be used for comparison with the information image data.

19. A non-transitory computer readable medium storing a program causing a processor of an image processing apparatus to execute a process for processing an image, the process comprising:
receiving sheet image data that is generated by reading an image on a medical record sheet onto which basic medical information and encoded information representing the basic medical information are printed, and extracting, from the sheet image data, information image data representing a portion where the basic medical information is printed;
generating reference image data representing the basic medical information, based on the encoded information represented in the sheet image data; and
detecting a correction that is to be performed on the basic medical information printed on the medical record sheet, based a difference between the information image data and the reference image data;
decoding information by decoding the encoded information; and
reproducing the reference image data from the decoded information in accordance with an expression condition to be used for comparison with the information image data.

* * * * *